US010539703B2

(12) United States Patent
Donadille et al.

(10) Patent No.: US 10,539,703 B2
(45) Date of Patent: Jan. 21, 2020

(54) METHOD AND SYSTEM FOR PETROPHYSICAL QUANTITY ESTIMATION FROM DIELECTRIC AND NEUTRON CAPTURE CROSS SECTION MEASUREMENTS

(71) Applicant: Schlumberger Technology Corporation, Sugar Land, TX (US)

(72) Inventors: Jean-Marc Donadille, Clamart (FR); Ishan Raina, Abu Dhabi (AE)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 554 days.

(21) Appl. No.: 15/343,241

(22) Filed: Nov. 4, 2016

(65) Prior Publication Data
US 2017/0176624 A1 Jun. 22, 2017

(30) Foreign Application Priority Data

Dec. 17, 2015 (EP) ..................................... 15290321

(51) Int. Cl.
*G01V 3/20* (2006.01)
*G01N 15/08* (2006.01)
*G01N 33/18* (2006.01)

(52) U.S. Cl.
CPC ............... *G01V 3/20* (2013.01); *G01N 15/08* (2013.01); *G01N 33/18* (2013.01)

(58) Field of Classification Search
CPC .......... G01V 3/20; G01V 11/00; G01N 33/18; G01N 15/08; E21B 47/00; E21B 49/00
See application file for complete search history.

(56) References Cited

U.S. PATENT DOCUMENTS

| 5,811,973 | A | 9/1998 | Meyer, Jr. | |
|---|---|---|---|---|
| 10,392,919 | B2* | 8/2019 | Peyaud | H04N 7/18 |
| 2007/0061082 | A1* | 3/2007 | Seleznev | G01V 3/26 |
| | | | | 702/11 |
| 2010/0283490 | A1 | 11/2010 | Minh et al. | |
| 2010/0327154 | A1* | 12/2010 | Vaeth | G01V 5/107 |
| | | | | 250/269.6 |
| 2012/0192640 | A1* | 8/2012 | Minh | E21B 7/06 |
| | | | | 73/152.16 |
| 2013/0002258 | A1* | 1/2013 | Ligneul | E21B 47/06 |
| | | | | 324/376 |

(Continued)

OTHER PUBLICATIONS

Schmitt, D.P., Al-Harbi, A., Saldungaray, P., Akkurt, R., and Zhang, T.: "Revisiting Dielectric Logging in Saudi Arabia: Recent Experiences and Applications in Development and Exploration Wells" paper SPE 149131 (18 pages).

(Continued)

*Primary Examiner* — Mohammad K Islam
(74) *Attorney, Agent, or Firm* — Sara K. M. Hinkley (57) ABSTRACT

A method includes receiving, via a processor, dielectric measurements of a geological formation and receiving, via the processor, sigma measurements. The sigma measurements include thermal neutron capture cross section of the geological formation. The method also includes jointly inverting to fit the dielectric measurements and the sigma measurements to a petrophysical model, and computing at least water salinity of the geological formation based on the joint inversion.

19 Claims, 6 Drawing Sheets

(56) References Cited

U.S. PATENT DOCUMENTS

| | | | | |
|---|---|---|---|---|
| 2013/0047717 A1* | 2/2013 | Gzara | ................. | G01V 5/10 |
| | | | | 73/152.03 |
| 2013/0204534 A1* | 8/2013 | Anand | ................. | G01V 3/38 |
| | | | | 702/11 |
| 2013/0206972 A1* | 8/2013 | Zhou | ................. | G01T 3/06 |
| | | | | 250/269.4 |
| 2013/0268201 A1* | 10/2013 | Gzara | ................. | G01V 9/00 |
| | | | | 702/8 |
| 2013/0338926 A1* | 12/2013 | Gzara | ................. | E21B 47/0003 |
| | | | | 702/8 |
| 2014/0129149 A1* | 5/2014 | Gzara | ................. | G01V 11/00 |
| | | | | 702/11 |
| 2014/0229112 A1* | 8/2014 | Datey | ................. | E21B 47/00 |
| | | | | 702/7 |
| 2014/0320126 A1* | 10/2014 | Heaton | ................. | G01V 11/00 |
| | | | | 324/303 |
| 2015/0015250 A1* | 1/2015 | Gzara | ................. | G01V 3/32 |
| | | | | 324/303 |

OTHER PUBLICATIONS

Donadille, J.M., Faivre, O.: "Water Complex Permittivity Model for Dielectric Logging" paper SPE 172566 (13 pages).
Extended European Search Report issued in the related EP Application 15290321.7, dated Jun. 29, 2016 (8 pages).

* cited by examiner

METHOD AND SYSTEM FOR PETROPHYSICAL QUANTITY ESTIMATION FROM DIELECTRIC AND NEUTRON CAPTURE CROSS SECTION MEASUREMENTS

CROSS-REFERENCE TO RELATED APPLICATIONS

The present invention claims the benefits of European Patent Application No. 15290321.7, filed on Dec. 17, 2015, titled "Method and System for Petrophysical Quantity Estimation from Dielectric and Neutron Capture Cross Section Measurements," the entire content of which is hereby incorporated by reference into the current application.

BACKGROUND

This disclosure relates to a method and system for estimating petrophysical quantities for a wide range of water salinity values in a subsurface formation.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Wells are generally drilled into a surface (land-based) location or ocean bed to recover natural deposits of oil and natural gas, as well as other natural resources that are trapped in geological formations. A well may be drilled using a drill bit attached to the lower end of a "drill string," which includes a drill-pipe, a bottom hole assembly, and other components that facilitate turning the drill bit to create a borehole. For oil and gas exploration and/or monitoring, it may be desirable to obtain information about the subsurface formations that are penetrated by a borehole for analysis. More specifically, this may include obtaining downhole measurements and estimating petrophysical quantities, such as water-filled porosity, water salinity, and/or water phase tortuosity, of the subsurface formations.

In some instances, dielectric measurements are obtained by a downhole tool and used to estimate the petrophysical quantities. However, many processes that are used to estimate the petrophysical quantities suffer from certain difficulties. For example, many processes that use the dielectric measurements alone may not solve for the water salinity when the salinity has values that are medium to high.

SUMMARY

This summary is provided to introduce a selection of concepts that are further described below in the detailed description. This summary is not intended to identify key or essential features of the subject matter described herein, nor is it intended to be used as an aid in limiting the scope of the subject matter described herein. Indeed, this disclosure may encompass a variety of aspects that may not be set forth below.

Systems and methods are provided for estimating petrophysical quantities, such as water-filled porosity, water salinity, and/or water phase tortuosity, for low, medium, and/or high values of water salinity in subsurface formations. An example of a method for estimating petrophysical quantities may include obtaining dielectric measurements at certain frequencies using a dielectric-measuring tool and thermal neutron capture cross section (referred to herein as "sigma") measurements using a sigma-measuring tool. The method may also include jointly inverting the dielectric measurements and sigma measurements to fit a petrophysical model (e.g., a dielectric model added to a sigma model). Using the dielectric measurements alone may not provide solutions for the water salinity when the salinity is medium to high values. However, the addition of the sigma measurements in the interpretation removes this difficulty. As a result of the joint inversion, the method may compute the water-filled porosity, water salinity, and/or water phase tortuosity even at medium to high values of water salinity.

An example of a system may include a well logging system that conveys a dielectric-measuring tool and a sigma-measuring tool into a wellbore of a formation and a data processing system. The dielectric-measuring tool and sigma-measuring tool may include various sensors that measure data and the data processing system may include a processor that receives the data. Example data may include dielectric measurements and sigma measurements. The processor may jointly invert the dielectric measurements and sigma measurements to fit a petrophysical model to compute the petrophysical quantities (e.g., water-filled porosity, water salinity, and/or water phase tortuosity) even at medium to high values of water salinity in the formation.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

One or more specific embodiments of the present disclosure will be described below. These described embodiments are examples of the presently disclosed techniques. Additionally, in an effort to provide a concise description of these embodiments, features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Some methods of salinity estimation using dielectric measurements alone suffer from difficulties at high values of the water salinity. For example, above a certain value of salinity, lines representing iso-salinity begin to cluster and become indistinguishable on generated overlays, as described in further detail below. Accordingly, some methods of salinity estimation may fix the salinity value to a best-guess value during inversion. As may be appreciated, fixing a best-guess value may bias the dielectric petrophysical model when the best-guess value is inaccurate. Thus, there is value to enhance salinity estimation at certain ranges of salinity values.

Accordingly, some embodiments of the present disclosure relate to systems and methods for robustly estimating the petrophysical quantities (e.g., water salinity, water-filled porosity, water phase tortuosity) from dielectric and sigma measurements even at medium to high values of water salinity. As described in detail below, the addition of the sigma measurements in the estimation of the petrophysical quantities removes the potential difficulty of obtaining estimations in medium- to high-salinity environments described above. In some embodiments, a dielectric-measuring tool and a sigma-measuring tool may be used to obtain dielectric measurements and sigma measurements, respectively. A data processing system may jointly invert the dielectric measurements and sigma measurements to compute the petrophysical quantities by fitting the measurements to a petrophysical model. Using the disclosed techniques may enable robust and accurate estimations of the petrophysical quantities for a wide range (e.g., low, medium, and high) of water salinity values, in contrast to some methods that solely use dielectric measurements.

It should be noted that the disclosed embodiments may be particularly beneficial for applications that use oil based mud (OBM) to drill, although the embodiments may be used for water based mud (WBM) drilling, as well. For example, determining characteristics of water in a formation may enable computing an amount of hydrocarbons present in the formation. The salinity of the water may provide insight into the hydrocarbon determination. The disclosed embodiments may enable accurate salinity estimation, among other petrophysical quantities, for the wide range of water salinity values.

Figure 1:
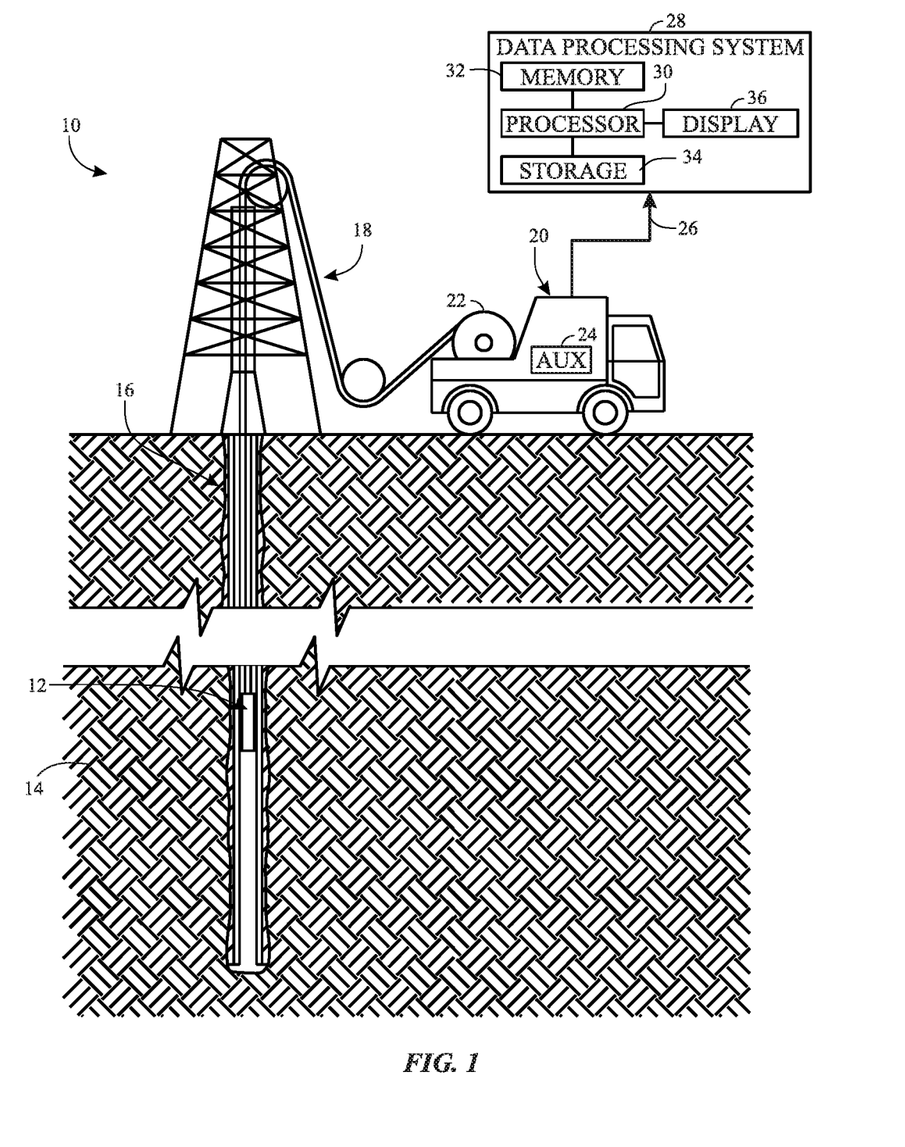
FIG. 1 is a schematic diagram of a well-logging system that employs a logging winch system, in accordance with an embodiment.

With this in mind, FIG. 1 illustrates a well-logging system 10 that may employ the petrophysical quantity estimation systems and methods of this disclosure. The well-logging system 10 may be used to convey a downhole tool 12 through a geological formation 14 via a wellbore 16. The downhole tool 12 is conveyed on a cable 18 via a logging winch system 20. Although the logging winch system 20 is schematically shown in FIG. 1 as a mobile logging winch system carried by a truck, the logging winch system 20 may be substantially fixed (e.g., a long-term installation that is substantially permanent or modular). Any suitable cable 18 for well logging may be used. The cable 18 may be spooled and unspooled on a drum 22 and an auxiliary power source 24 may provide energy to the logging winch system 20 and/or the downhole tool 12.

Although the downhole tool 12 is described as a wireline downhole tool, it should be appreciated that any suitable conveyance may be used. For example, the downhole tool 12 may instead be conveyed as a logging-while-drilling (LWD) tool as part of a bottom hole assembly (BHA) of a drill string, conveyed on a slickline or via coiled tubing, and so forth. For the purposes of this disclosure, the downhole tool 12 may be any suitable measurement tool that uses sensors to obtain dielectric measurements or sigma (thermal neutron cross capture) measurements of the wellbore 16 wall.

For example, the downhole tool 12 may be a dielectric-measuring tool that obtains electromagnetic measurements. Additionally, the downhole tool 12 may be a sigma-measuring tool that obtains sigma measurements. Accordingly, although one downhole tool 12 is illustrated, it should be noted that any suitable number of downhole tools 12 may be used to accomplish the disclosed techniques. For example, a first downhole tool 12 that includes the dielectric-measuring tool may measure a volume of the geological formation 14 to obtain the dielectric measurements, and a second downhole tool 12 that includes the sigma-measuring tool may measure the same volume of the geological formation 14 to obtain the sigma measurements. In some embodiments, a single downhole tool 12 that includes both the dielectric-measuring tool and the sigma-measuring tool may be used to measure the same volume of the geological formation 14.

As discussed further below, the downhole tool 12 may include a number of radiation sources or electromagnetic transmitters and a number of detectors or receivers used to acquire data 26 about the wellbore 16 and/or geological formation 14 by taking measurements. The data 26 may be sent to a data processing system 28. The data processing system 28 may analyze the data 26 to compute petrophysical quantities, such as water-filled porosity, water salinity, and/or water phase tortuosity, by jointly inverting the dielectric measurements and the sigma measurements to fit a petrophysical model. The data processing system 28 may be any electronic data processing system that can be used to carry out the systems and methods of this disclosure. For example, the data processing system 28 may include a processor 30, which may execute instructions stored in memory 32 and/or storage 34. As such, the memory 32 and/or the storage 34 of the data processing system 28 may be any suitable article of manufacture that can store the instructions. The memory 32 and/or the storage 34 may be ROM memory, random-access memory (RAM), flash memory, an optical storage medium, or a hard disk drive, to name a few examples. A display 36, which may be any suitable electronic display, may display the overlays described below and/or the computed petrophysical quantities generated by the processor 30. The data processing system 28 may be a local component of the logging winch system 20, a remote device that analyzes data from other logging winch systems 20, or partly local and partly remote. In some embodiments, the data processing system 28 may be a mobile computing device (e.g., tablet, smartphone, or laptop) or a server remote from the logging winch system 20.

Figure 2:
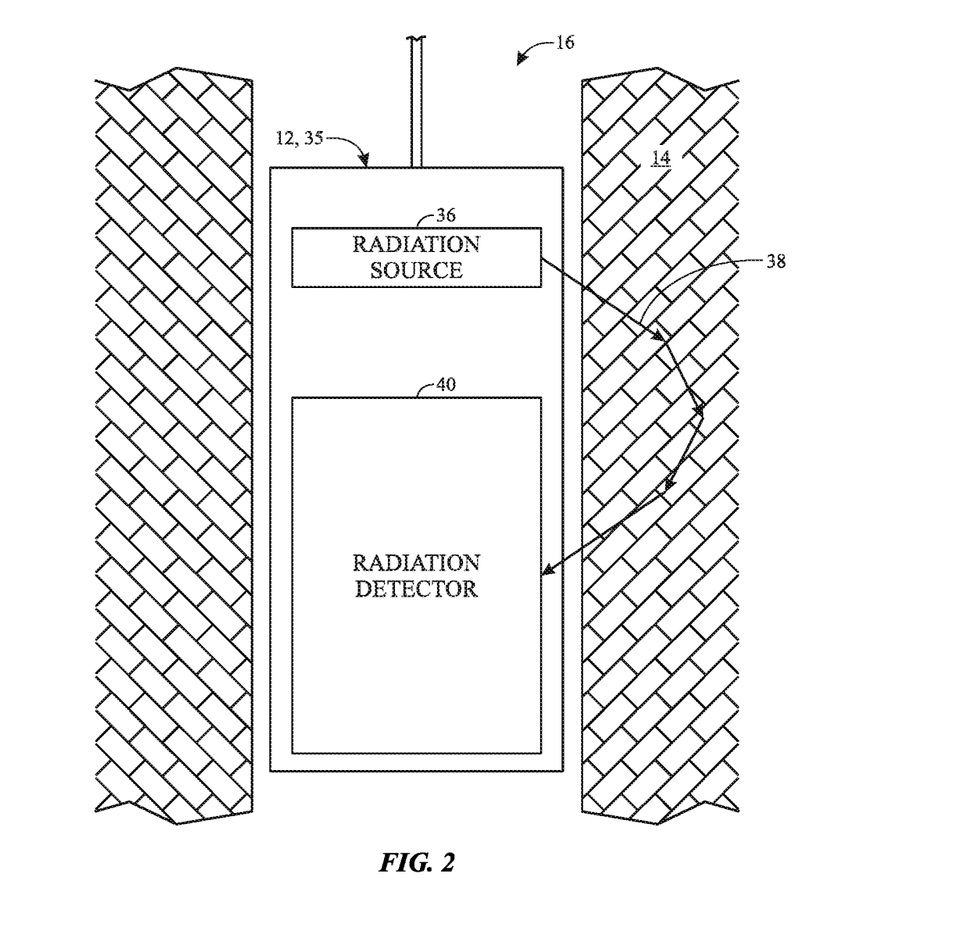
FIG. 2 is a block diagram of one example of the downhole tool used by the well-logging system of FIG. 1, in accordance with an embodiment.

FIG. 2 is a block diagram of one example of the downhole tool 12 used by the well-logging system 10 of FIG. 1, in accordance with an embodiment. In the illustrated example, the downhole tool 12 is a sigma (e.g., thermal neutron capture cross section) measuring tool 35 capable of obtaining sigma measurements of the formation volume of interest. As depicted, the sigma-measuring tool 35 may include a radiation source 36 to emit radiation 38 into the geological formation 14. The radiation source 36 may include, for example, a radioisotopic gamma-ray source (e.g., Cs or Am) or an electronic x-ray generator, and/or a radio isotopic or electronic neutron-generator. The radiation source 36 emits radiation 38 out of the sigma-measuring tool 35. For example, the radiation 38 may enter the geological formation 14, where it may scatter or collide with atoms of the geological formation 14 to generate other radiation that may scatter. Some of the radiation 38 or radiation that results from interactions with the radiation 38 in the geological formation 14 may scatter and return to the sigma-measuring tool 35 to be detected by a radiation detector 40. In general, the radiation detector 40 may detect when ionizing radiation enters the sigma-measuring tool 35 and generate an electrical signal, such as a count rate of detected radiation or spectrum of detected radiation that may provide an indication of characteristics of the wellbore 16 or the geological formation 14. For example, the electrical signal may represent the sigma measurements. The sigma measurements may be delivered to the data processing system 28 via a telemetry system that may include the transmissions over the cable 18 or wirelessly.

Figure 3:
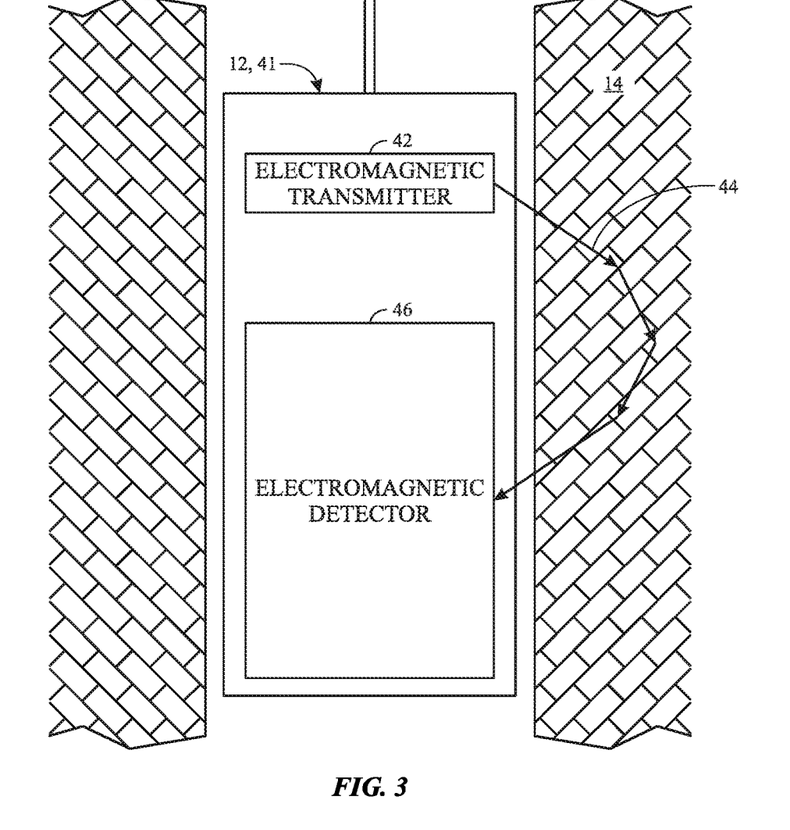
FIG. 3 is a block diagram of another example of the downhole tool used by the well-logging system of FIG. 1, in accordance with an embodiment.

FIG. 3 is a block diagram of another example of the downhole tool 12 used by the well-logging system 10 of FIG. 1, in accordance with an embodiment. In the illustrated example, the downhole tool 12 is a dielectric-measuring tool 41 capable of obtaining dielectric measurements of the formation volume of interest. In some embodiments, the dielectric measurements may include permittivity and conductivity. Further, the dielectric-measuring tool 41 may perform any number of measurements at differing frequencies. For example, in some embodiments, permittivity and conductivity measurements may be obtained at four different operational frequencies, thereby resulting in eight measurements total. The four frequencies (e.g., F0, F1, F2, and F3) may increase from a lowest frequency F0 to a highest frequency F3 (e.g., between about 20 MHz to 1 GHz).

As depicted, the dielectric-measuring tool 41 may include a transmitter 42 that emits a signal 44 through the formation 14 to a receiver 46. The transmitter 42 and receiver 46 may be configured to obtain dielectric measurements using electromagnetic propagation. Although just one transmitter 42 and receiver 46 are shown, it should be noted that any suitable number (e.g., 1, 2, 3, 4, 5, 6, 7, 8, etc.) of transmitters 42 and any suitable number (e.g., 1, 2, 3, 4, 5, 6, 7, 8, etc.) of receivers 46 may be used. In some embodiments, certain of the transmitters 42 may be configured to emit signals at differing frequencies (e.g., 20 MHz to 1 GHz). Since the frequencies are relatively high, the depth of investigation into the formation 14 may be relatively shallow (e.g., one to ten inches). Also, the relatively high frequencies may reduce the electrical impedance of OBM. The transmitters 42 and receivers 46 may include antennas having collocated longitudinal and transverse polarizations. Additionally, the transmitters 42 and receivers 46 may be spaced apart to provide different depth readings. Further, the transmitters 42 and the receivers 46 may be arranged on a pad that provides three-axis articulated movement. The data obtained by the receiver 46 may be delivered to the data processing system 28 via a telemetry system that may include the transmissions over the cable 18 or wirelessly.

Figure 4:
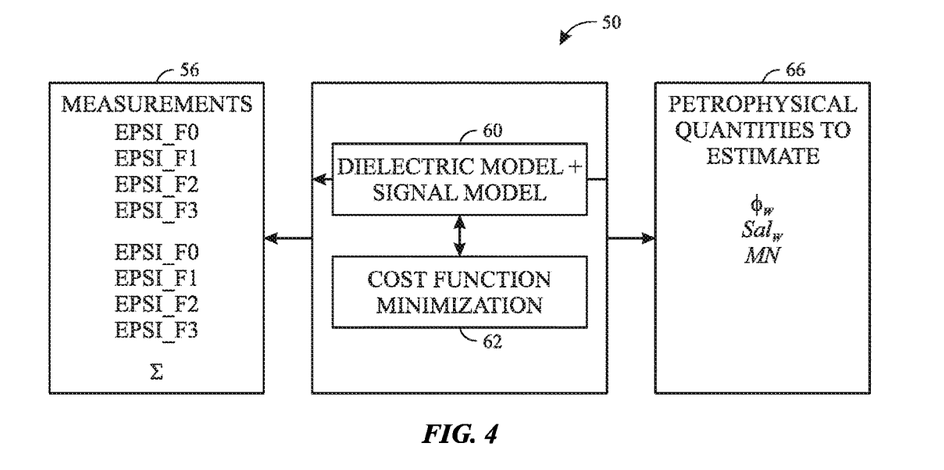
FIG. 4 is a block diagram of a method for computing petrophysical quantities even at medium to high water salinity values by jointly inverting dielectric measurements and sigma measurements, in accordance with an embodiment.
Figure 5:
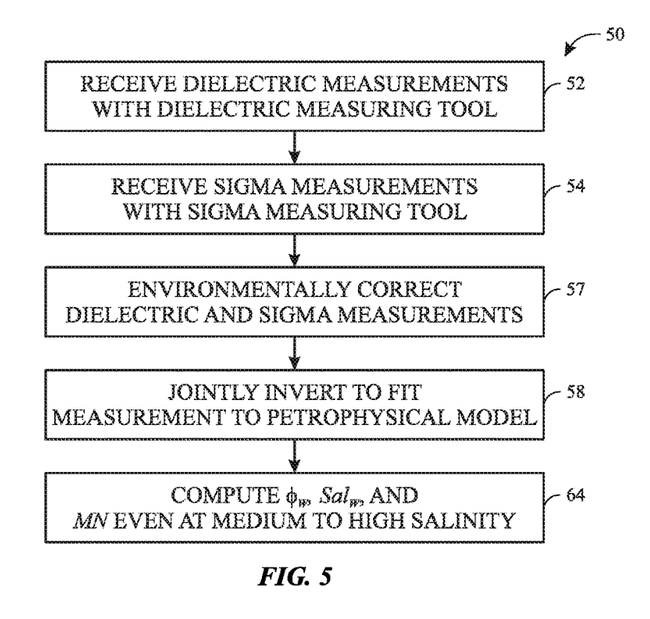
FIG. 5 is a flowchart of the method of FIG. 4, in accordance with an embodiment.

FIG. 4 is a block diagram of a method 50 for computing petrophysical quantities even at medium to high water salinity values by jointly inverting dielectric measurements and sigma measurements, in accordance with an embodiment. FIG. 5 is a flowchart of the method 50 of FIG. 4, in accordance with an embodiment. For clarity, FIG. 4 and FIG. 5 are discussed together below.

Although the following description of the method 50 is described as being performed by the processor 30 of the data processing system 28, it should be noted that the method 50 may be performed by other processors disposed on other devices that may be capable of communicating with the data processing system 28, the dielectric-measuring tool 41, and/or the sigma-measuring tool 35, such as a computing device or other component associated with the well-logging system 10. Additionally, although the following method 50 describes a number of operations that may be performed, it should be noted that the method 50 may be performed in a variety of suitable orders and some of the operations may not be performed. It should be appreciated that the method 50 may be wholly executed by the data processing system 28 or the execution may be distributed between another computing device (e.g., downhole tool 12) and the data processing system 28. It should be noted that the method 50 may be implemented as computer instructions stored on the memory 38 and/or storage 40.

Referring now to the method 50, the processor 30 may receive (block 52) dielectric measurements from the dielectric-measuring tool 41 and receive (block 54) sigma measurements from the sigma-measuring tool 35. As depicted, measurements 56 may include four permittivity measurements at four different frequencies (EPSI_F0, EPSI_F1, EPSI_F2, EPSI_F3) and four conductivity measurements at four different frequencies (COND_F0, COND_F1, COND_F2, COND_F3). Further, the measurements 56 may also include the sigma measurements ($\Sigma$). The processor 30 may environmentally correct (block 57) the dielectric measurements and the sigma measurements by processing the raw measurements to remove effects of the borehole and mudcake so that the processed measurements 56 are more representative of the actual physical properties of the formation (e.g., formation permittivity, conductivity, and sigma). Once environmentally corrected, the processor 30 may use the processed nine input measurements 56 to perform a joint dielectric-sigma inversion procedure (block 58) to fit the measurements 56 to a petrophysical model 60. However, in some embodiments, some of the inputs may not be used. For example, in some embodiments, just the permittivity and sigma measurements may be used in the inversion procedure or just the conductivity and sigma measurements may be used in the inversion procedure.

The petrophysical model 60 may include a dielectric model combined with a sigma model. This offers the possibility of using any dielectric petrophysical model in the inversion, and inverting for the water phase tortuosity MN too. Example dielectric models that may be used include complex refractive index method (CRIM), Stroud-Milton-De (SMD), Bimodal, or the like, as described in detail below. The sigma model may use a volumetric equation or any suitable variation, as described in detail below. The processor 30 may also minimize a cost function 62 when fitting the measurements to the petrophysical model 60. The cost function may include any suitable function, such as a multi-variable function, an algebraic sum function, a sum of the squares function, or the like. The processor 30 may compute (block 64) certain petrophysical quantities 66, such as the water-filled porosity ($\phi_w$), the water salinity ($Sal_w$), and/or the water phase tortuosity (MN) even at medium- to high-salinity values, after the measurements 56 are jointly inverted.

Figure 6:
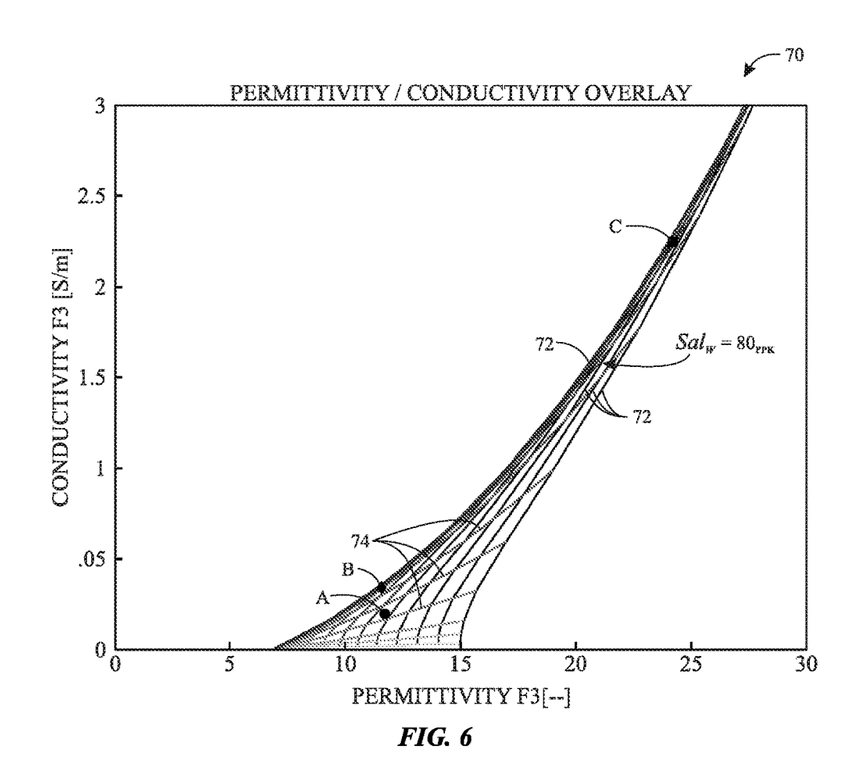
FIG. 6 is a permittivity and conductivity overlay generated using dielectric measurements at a particular frequency, in accordance with an embodiment.

FIG. 6 is a permittivity and conductivity overlay 70 generated using dielectric measurements at a particular frequency, in accordance with an embodiment. The overlay 70 may be generated as part of the joint inversion (block 58) step of the method 50. The overlay 70 may be generated by the processor 30 through the inversion of a dielectric petrophysical model using the dielectric measurements consisting of permittivity and conductivity at the highest frequency (F3). However, it should be noted that the overlay 70 may be generated for the permittivity and conductivity at any other suitable frequency. The overlay 70 of the formation permittivity ε (x-axis) and conductivity σ (y-axis) was generated using the CRIM model. However, as noted above, any other suitable model, such as SMD, Bimodal, or the like, may produce a similar overlay 70. The CRIM model may be calculated in accordance with the following relationship:

$$\sqrt{\varepsilon + i\frac{\sigma}{\omega\varepsilon_0}} = (1-\phi_T)\sqrt{\varepsilon_{mtx}} + (\phi_T - \phi_w)\sqrt{\varepsilon_{hc}} + \phi_w\sqrt{\varepsilon_w(Sal_w, T, P)}$$

Equation (1)

Where ω denotes the angular frequency of operation, i is the imaginary unit defined as $\sqrt{-1}=1$, $\varepsilon_0$ is the free space permittivity (fixed value), and $\varepsilon_w$ is the complex permittivity of water, which depends on salinity, temperature, and pressure. Further, the following values for the respective parameters were used to produce the overlay 70; however, any suitable values may be used:

Total porosity $\phi_T$=0.2 [m³/m³]
Matrix permittivity $\varepsilon_{mtx}$=8.5 [ ], corresponding to limestone
Hydrocarbon permittivity $\varepsilon_{hc}$=2.2 [ ], corresponding to oil
Temperature T=200 [degF]
Pressure P=10,000 [PSI]

The overlay 70 is shown in terms of darker lines 72 that represent equal water-filled porosity, and lighter lines 74 that represent equal water salinity. The Iso-$\phi_w$ (water-filled porosity) values are: {0, 0.02, 0.04, 0.06, 0.08, 0.10, 0.12, 0.14, 0.16, 0.18, and 0.20} [m³/m³]. The Iso-$Sal_w$ (water salinity) values are: {0.5, 1.5, 3, 7, 15, 30, 70, 110, 150, 200, 250, and 300} [ppk]. For both of the petrophysical quantities, the clearest lines (e.g., most spaced apart) correspond to the lowest values. As may be appreciated from the overlay 70, above a certain value of salinity (e.g., around 80 parts per thousand (ppk)), the iso-salinity lines 74 become clustered together, thereby rendering the lines 74 indistinguishable and difficult to estimate the salinity based on the dielectric data alone. The processor 30 may solve for equal water-filled porosity for lines 72 that show at least some separation (e.g., for large enough water-filled porosity). As previously mentioned, in some processes, because of the difficulty caused by the salinities clustering, the processor 30 may fix the salinity to a best-guess value in the inversion. It should be noted that the salinity lines 74 cluster at an even lower salinity value on the lower frequency overlays. Accordingly, as described herein, embodiments of the present approach use the sigma measurements and jointly invert the measurements using a sigma model in conjunction with the dielectric model enables estimating the salinity values at the medium to high salinity range.

Three points are identified on the overlay 70 that correspond to:
Point A (circle): $\phi_w$=0.11; $Sal_w$=10 ppk
Point B (diamond): $\phi_w$=0.05; $Sal_w$=110 ppk
Point C (square): $\phi_w$=0.15; $Sal_w$=220 ppk As point A is in a fairly open region of the overlay 70, both its water-filled porosity and salinity can be robustly estimated from the dielectric data inversion. In contrast, it is clear that the salinity of points B and C cannot be estimated because the salinity lines 74 are too closely clustered. However, the water-filled porosity for points B and C may be estimated with the salinity being fixed, albeit not very robustly.

To compensate for the difficulty in determining medium- to high-salinities using just dielectric measurements, the sigma measurements may be included in the joint inversion using the petrophysical model 60. The sigma measurement has a good sensitivity to water salinity at high salinity values and to the water-filled porosity. An additional benefit of using the sigma measurement is that the sigma-measuring tool 35 reads a comparable volume of formation as the dielectric tool 41. Accordingly, using both tools in a joint interpretation targets a well-defined zone in the formation 14. For example, the depth of investigation of the sigma-measuring tool 35 may be approximately seven inches, and the depth of investigation of the dielectric-measuring tool 41 may be approximately four to five inches. The processor may robustly estimate the petrophysical quantities even at medium to high values of salinity by jointly inverting the consonant dielectric (ε and σ) and sigma (Σ) measurements 56. Then, the resolution for water-filled porosity and water salinity from the combination of measurements can be visualized by adding up the information from the conductivity/permittivity overlay 70 with a permittivity/sigma overlay (FIG. 7) and/or a conductivity/sigma overlay (FIG. 8).

Figure 7:
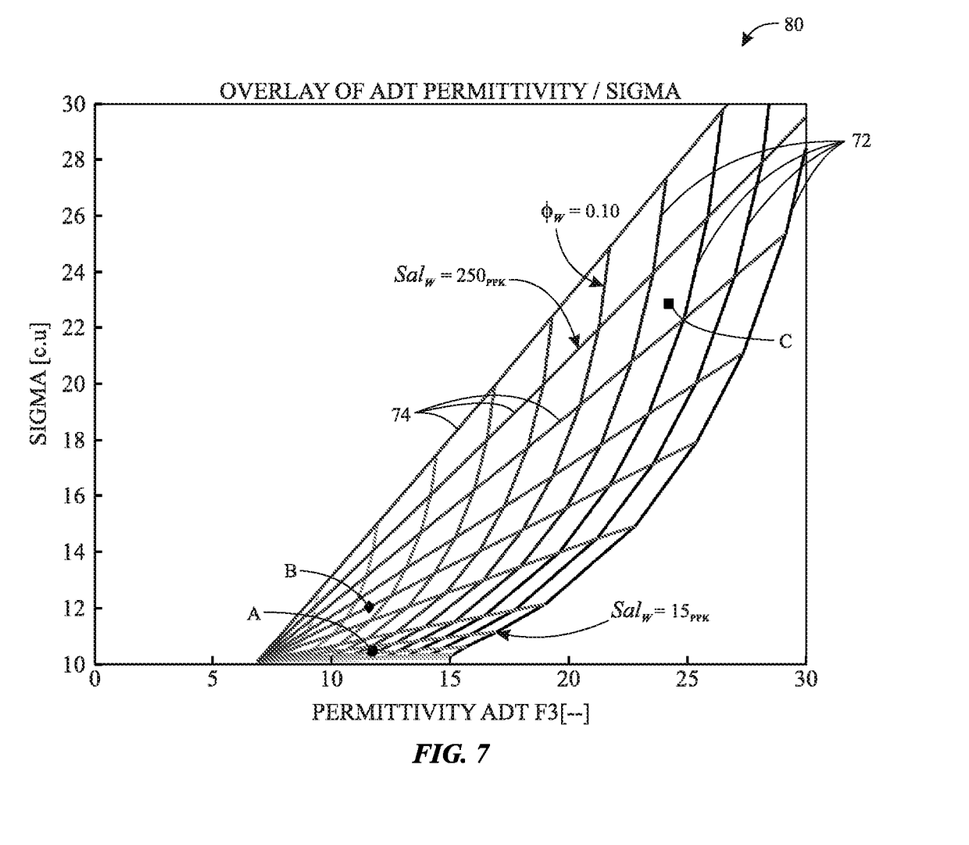
FIG. 7 is a permittivity and sigma overlay generated using dielectric measurements at a particular frequency and sigma measurements, in accordance with an embodiment.
Figure 8:
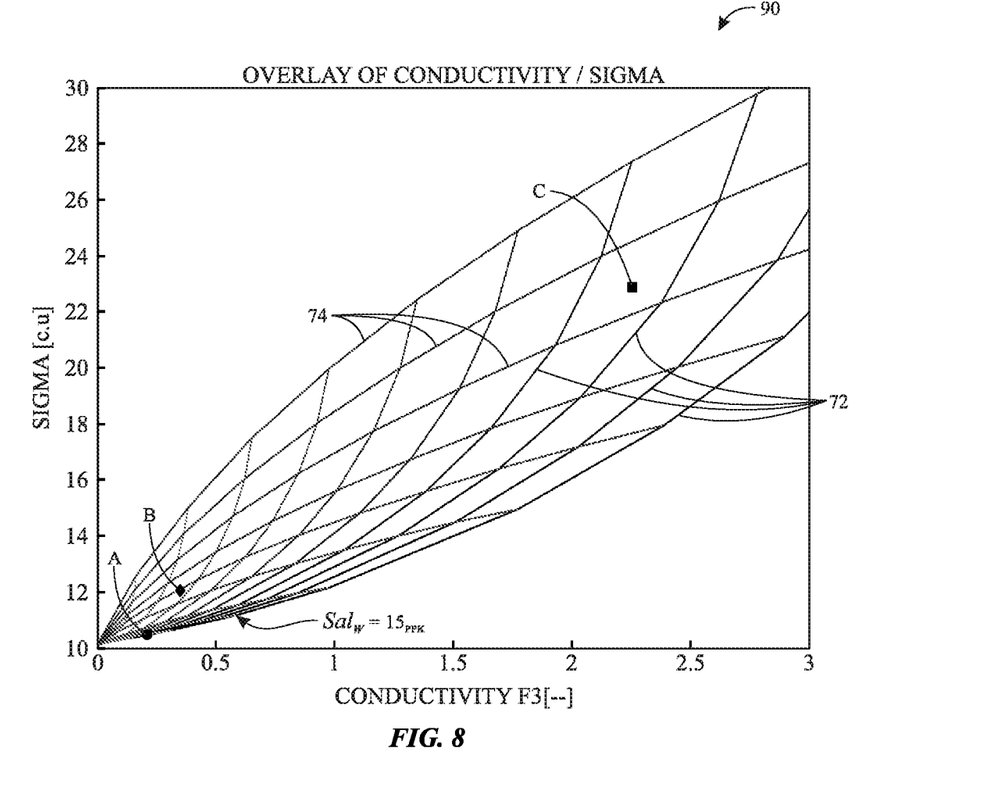
FIG. 8 is a conductivity and sigma overlay generated using dielectric measurements at a particular frequency and sigma measurements, in accordance with an embodiment.

FIG. 7 is a permittivity and sigma overlay 80 generated using dielectric measurements at a particular frequency and sigma measurements, in accordance with an embodiment. The overlay 80 may be generated as part of the joint inversion (block 58) step of the method 50. For example, the permittivity measurements and the sigma measurements may be jointly inverted to fit the petrophysical model 60, which includes the dielectric model, such as the CRIM model (or any suitable model) described above, combined with the sigma model, described below. As depicted, the overlay 80 is generated using permittivity measurements taken at the highest frequency (F3), but it should understood that the overlay 80 may be generated for permittivity measurements at any other suitable frequency.

Turning now to the overlay 80, the dielectric permittivity (x-axis) is generated using the dielectric model described in FIG. 6. The neutron formation sigma (y-axis) is linked to the water-filled porosity and salinity through a sigma model that includes a volumetric equation expressed by the following relationship:

$$\Sigma = (1\phi_T)\Sigma_{mtx} + (\phi_T\phi_w)\Sigma_{hc} + \phi_w\Sigma_w(\text{Sal}_w, T, P) \quad \text{Equation (2)}$$

Where the dependency of the water neutron capture cross section to salinity, temperature, and pressure is represented by the following relationships:

$$\begin{cases} \sum_w (Sal_w, T, P) = \alpha(T, P) \sum_{w,unc} (Sal_w) \\ \alpha(T, P) = 1 + 2.8 \ 10^{-6}(P14.7)3.3 \ 10^{-4}(T68) \\ \sum_{w,unc} (Sal_w) = 22.727 + 3.2575 \ 10^{-1} Sal_w + 3.0025 \ 10^{-4} Sal_w^2 \end{cases}$$

Equations (3), (4), and (5), from top to bottom

Further, the following values for the respective parameters were used to produce the overlay 80; however, any suitable values may be used:

Total porosity $\phi_T$=0.2

$$\left[\frac{m^3}{m^3}\right]$$

Matrix permittivity $\varepsilon_{mtx}$=8.5 [ ], corresponding to limestone
Matrix Sigma $\Sigma_{mtx}$=7.1 [c.u], corresponding to limestone
Hydrocarbon permittivity $\varepsilon_{hc}$=2.2 [ ], corresponding to oil
Hydrocarbon Sigma $\Sigma_{hc}$=22 [c.u], corresponding to oil
Temperature T=200 [degF]
Pressure P=10,000 [PSI]

The values of the equal water-filled porosity lines 72 and equal salinity lines 74 are the same as in FIG. 6. The overlay 80 of FIG. 7 is clearly more open than the overlay 70 in FIG. 6 in the high-salinity region. Conversely the iso-salinity lines 74 tend to get clustered at low salinity in the sigma and permittivity overlay 80. This is physically due to the sigma measurement being primarily sensitive to the salt content. This complementary sensitivity of the sigma measurement (with respect to the dielectric measurement) makes the dielectric-sigma measurement combination an exceptional one for estimating the water salinity (and water-filled porosity) across the wide range (e.g., 0.1 ppk to 300 ppk) of salinities. This may be illustrated with the three sample points A, B, and C:

Point A (circle): (low salinity) lies in a fairly busy region (lines 72 and 74 clustered together) in FIG. 7. The addition of the sigma measurement does not provide much help in resolving the salinity of this point. However, FIG. 6 showed that dielectric alone could clearly resolve both the water-filled porosity and water salinity for this point at this range of salinity.

Point B (diamond): (medium salinity) lies in an open region (lines 72 and 74 reasonably spaced apart) in FIG. 7. The spacing of the lines 72 and 74 is due to the addition of the sigma with the dielectric. The dielectric-sigma combination may now robustly resolve both the water-filled porosity and water salinity of points having medium salinity.

Point C (square): (high salinity): lies in an even more open region (lines 72 and 74 spaced apart even further than at point B) in FIG. 7. The spacing of the lines 72 and 74 is due to the addition of the sigma with the dielectric. The dielectric-sigma combination may now robustly resolve both the water-filled porosity and water salinity of points having high salinity.

For completeness, the conductivity ($\sigma$) and sigma ($\Sigma$) overlay is shown below for the same values of the parameters.

FIG. 8 is a conductivity and sigma overlay 90 generated using dielectric measurements at a particular frequency and sigma measurements, in accordance with an embodiment. The overlay 90 may be generated as part of the joint inversion (block 58) step of the method 50. For example, the conductivity measurements and the sigma measurements may be jointly inverted to fit the petrophysical model 60, which includes the dielectric model, such as the CRIM model (or any suitable model) described above, combined with the sigma model, also described above. As depicted, the overlay 90 is generated using conductivity measurements taken at the highest frequency (F3), but it should understood that the overlay 90 may be generated for conductivity measurements at any other suitable frequency.

The values of the equal water-filled porosity lines 72 and equal salinity lines 74 are the same as in FIG. 6. The overlay 90 of FIG. 8 is clearly more open than the overlay 70 in FIG. 6 in the high-salinity region. Conversely the iso-salinity lines 74 tend to get clustered at low salinity in the sigma and permittivity overlay 80 similar to the permittivity and sigma overlay 80 of FIG. 7. Points A, B, and C are located in similar regions as in the permittivity and sigma overlay 80 of FIG. 7. That is, point A (circle) lies in a low salinity region where the lines 72 and 74 are clustered together, thereby rendering resolution of the salinity at this point difficult. However, FIG. 6 showed that dielectric alone could clearly resolve both the water-filled porosity and water salinity for this point at this range of salinity. Point B (diamond) lies in a medium salinity region where the lines 72 and 74 are reasonably spaced apart in FIG. 8. The spacing of the lines 72 and 74 is due to the addition of the sigma with the dielectric. The dielectric-sigma combination may now robustly resolve both the water-filled porosity and water salinity of points having medium salinity. Lastly, point C lies in the high salinity region where the lines 72 and 74 spaced apart even further than at point B in FIG. 8. The spacing of the lines 72 and 74 is due to the addition of the sigma with the dielectric. The dielectric-sigma combination may now robustly resolve both the water-filled porosity and water salinity of points having high salinity.

It should be appreciated that the conductivity and sigma overlay 90 enables robust estimations for water salinity and water-filled porosity of medium and high values of salinity similar to the permittivity and sigma overlay 80 of FIG. 7. Thus, in some embodiments, petrophysical quantities 66 may be computed for a wide range of water salinity values when either the permittivity and sigma overlay 80 or the conductivity and sigma overlay 90 are combined with the dielectric (permittivity and conductivity) overlay 70. Additionally or alternatively, the three of the overlays 70, 80 and 90 may be combined to ascertain the petrophysical quantities 66.

The specific embodiments described above have been shown by way of example, and it should be understood that these embodiments may be susceptible to various modifications and alternative forms. It should be further understood that the claims are not intended to be limited to the particular forms discloses, but rather to cover modifications, equivalents, and alternatives falling within the spirit of this disclosure.

The invention claimed is:

1. A method comprising:
receiving, via a processor, dielectric measurements of a geological formation; receiving, via the processor, sigma measurements, wherein the sigma measurements comprise thermal neutron capture cross section of the geological formation;
environmentally correcting the dielectric measurements and the sigma measurements;
jointly inverting to fit the corrected dielectric measurements and the corrected sigma measurements to a petrophysical model; and
computing at least water salinity of the geological formation and computing the water phase tortuosity for medium to high range of water salinity values in a subsurface formation based on the joint inversion.

2. The method of claim 1, wherein jointly inverting to fit the dielectric measurements and the sigma measurements to the petrophysical model results in a permittivity and conductivity overlay, a permittivity and sigma overlay, a conductivity and sigma overlay, or both that are used to compute at least the water salinity of the geological formation for a wide range of values of water salinity.

3. The method of claim 1, wherein the petrophysical model comprises a dielectric model combined with a sigma model.

4. The method of claim 3, wherein the dielectric model is calculated in accordance with the following relationship:

$$\sqrt{\varepsilon + i\frac{\sigma}{\omega\varepsilon_0}} = (1 - \phi_T)\sqrt{\varepsilon_{mtx}} + (\phi_T - \phi_w)\sqrt{\varepsilon_{hc}} + \phi_w\sqrt{\varepsilon_w^*(Sal_w, T, P)},$$

where $\varepsilon$ is permittivity, i is the imaginary unit defined as $\sqrt{i}=-1$, $\sigma$ is conductivity, $\omega$ is angular frequency of operation, $\varepsilon_0$ is free space permittivity, $\varepsilon_w^*$ is complex permittivity of water, $Sal_w$ is water salinity, T is temperature, P is pressure, $\phi_T$ is total porosity, $\phi_w$ is water-filled porosity, and $\varepsilon_{mtx}$ is matrix permittivity, and $\varepsilon_{hc}$ is hydrocarbon permittivity.

5. The method of claim 3, wherein the sigma model is calculated in accordance with the following relationship:

$$\Sigma = (1-\phi_T)\Sigma_{mtx} + (\phi_T-\phi_w)\Sigma_{hc} + \phi_w\Sigma_w(Sal_w, T, P),$$

where $Sal_w$ is water salinity, $\phi_T$ is total porosity, $\phi_w$ is water-filled porosity, $\Sigma_{mtx}$ is matrix sigma, $\Sigma_{hc}$ is hydrocarbon sigma, $\Sigma_w$ is water sigma, T is temperature, and P is pressure.

6. The method of claim 5, wherein the dependency of water sigma to salinity, temperature, and pressure is calculated in accordance with the following relationships:

$$\begin{cases} \sum_w (Sal_w, T, P) = \alpha(T, P) \sum_{w,unc} (Sal_w) \\ \alpha(T, P) = 1 + 2.8 \cdot 10^{-6}(P14.7)3.3 \cdot 10^{-4}(T68) \\ \sum_{w,unc} (Sal_w) = 22.727 + 3.2575 \cdot 10^{-1} Sal_w + 3.0025 \cdot 10^{-4} Sal_w^2, \end{cases}$$

where $\Sigma_{w,unc}$ is the water sigma uncorrected for temperature and pressure effects, and $\alpha$ is the temperature and pressure correction coefficient for the water sigma.

7. The method of claim 1, wherein the dielectric measurements are collected from a dielectric-measuring tool investigating a volume of the geological formation and the sigma measurements are collected from a sigma-measuring tool investigating the same volume of the geological formation.

8. The method of claim 1, comprising computing the water-filled porosity for a wide range of water salinity values based on the joint inversion.

9. The method of claim 1, wherein the dielectric measurements comprise permittivity measurements at a plurality of frequencies, conductivity measurements at a plurality of frequencies, or both.

10. The method of claim 1, wherein low water salinity values are resolved by fitting the dielectric measurements to the petrophysical model and the medium to high water salinity values are resolved by fitting the dielectric measurements and sigma measurements to the petrophysical model.

11. A system, comprising:
a dielectric-measuring tool configured to obtain dielectric measurements; a sigma-measuring tool configured to obtain thermal neutron capture cross section measurements;
a data comprising a processor configured to:
receive dielectric measurements of a geological formation;
receive sigma measurements, wherein the sigma measurements comprise thermal neutron capture cross section of the geological formation;
environmentally correct the dielectric measurements and the sigma measurements;
jointly invert to fit the corrected dielectric measurements and the corrected sigma measurements to a petrophysical model; and
compute water salinity and water phase tortuosity for medium to high range of water salinity values in a subsurface formation based on the joint inversion.

12. The system of claim 11, wherein the dielectric measurements and the sigma measurements relate to the same volume of the geological formation.

13. The system of claim 11, wherein jointly inverting to fit the dielectric measurements and the sigma measurements to the petrophysical model results in a permittivity and conductivity overlay, a permittivity and sigma overlay, a conductivity and sigma overlay, or both that are used to compute at least the water salinity of the geological formation for the wide range of values of water salinity.

14. The system of claim 11, wherein the dielectric measurements comprise permittivity measurements at a plurality of frequencies in the range of 20 MHz to 1 GHz, conductivity measurements at a plurality of frequencies in the range of 20 MHz to 1 GHz, or both.

15. The system of claim 11, wherein the petrophysical model comprises a combination of a dielectric model and a sigma model.

16. The system of claim 11, wherein computed for the water salinity values between 0.1 part per thousand (ppk) and 300 ppk.

17. A tangible, non-transitory computer-readable medium storing instructions that, when executed by a processor, cause the processor to:

receive dielectric measurements and sigma measurements, wherein the sigma measurements comprise thermal neutron capture cross section of a geological formation;
environmentally correct the dielectric measurements and the sigma measurements;
jointly invert the corrected dielectric measurements and the corrected sigma measurements to fit a petrophysical model comprising a dielectric model and a sigma model;
compute at least water salinity and water tortuosity for medium to high-range of water salinity values in a subsurface formation based on the joint inversion using the petrophysical model.

18. The computer-readable medium of claim 17, wherein the instructions, when executed by the processor, cause the processor to compute water-filled porosity using the dielectric model.

19. The computer-readable medium of claim 18, wherein the instructions, when executed by the processor, cause the processor to compute at least water salinity and water-filled porosity for a wide range of water salinity values based on the joint inversion using the petrophysical model by generating a permittivity and conductivity overlay used to compute low values of water salinity and genearintg a permittivity and sigma overlay, a conductivity and sigma overlay, or both used to compute medium to high values of water salinity.

* * * * *